United States Patent [19]
Doran et al.

[11] Patent Number: 5,393,900
[45] Date of Patent: Feb. 28, 1995

[54] STEROID INTERMEDIATES FOR THE FORMATION OF VITAMIN $D_3$ ANALOGUES

[75] Inventors: Thomas I. Doran, West Orange, N.J.; John A. McLane, New Haven, Conn.; Masami Okabe, Nutley, N.J.; Michelangelo Scalone, Birsfelden, Switzerland; Milan R. Uskokovic, Upper Montclair, N.J.

[73] Assignee: Hoffmann-La Roche inc., Nutley, N.J.

[21] Appl. No.: 255,012

[22] Filed: Jun. 7, 1994

Related U.S. Application Data

[60] Division of Ser. No. 155,663, Nov. 22, 1993, Pat. No. 5,342,833, which is a continuation of Ser. No. 979,133, Nov. 20, 1992, abandoned.

[51] Int. Cl.⁶ ................................................. C07J 9/00
[52] U.S. Cl. .................................... 552/505; 552/546
[58] Field of Search ............................ 552/505, 546

[56] References Cited

U.S. PATENT DOCUMENTS

| | | | |
|---|---|---|---|
| 3,970,676 | 7/1976 | Salmond | 260/397.2 |
| 4,116,985 | 9/1978 | Salmond | 260/397.2 |
| 4,360,471 | 11/1982 | DeLuca et al. | |
| 4,448,721 | 5/1984 | DeLuca | 260/239.5 |
| 4,456,553 | 6/1984 | Oshida et al. | 260/397.2 |
| 4,804,502 | 2/1989 | Baggiolini et al. | |
| 5,087,619 | 2/1992 | Baggiolini et al. | |
| 5,145,846 | 9/1992 | Baggiolini et al. | |
| 5,206,230 | 4/1993 | Ikekawa et al. | |
| 5,218,109 | 6/1993 | Tsuji et al. | 540/4 |

FOREIGN PATENT DOCUMENTS

| | | |
|---|---|---|
| 0321572 | 6/1989 | European Pat. Off. |
| 0325279 | 7/1989 | European Pat. Off. |
| 386793 | 3/1990 | European Pat. Off. |
| 387077 | 3/1990 | European Pat. Off. |
| 0377743 | 7/1990 | European Pat. Off. |
| 0398217 | 11/1990 | European Pat. Off. |
| WO91/03246 | 3/1991 | WIPO |
| WO9214746 | 9/1992 | WIPO |

OTHER PUBLICATIONS

Malloy, et al., The Journal of Investigative Dermatology, Mar. 1989, vol. 92, No. 3 p. 475.
The Journal of Nutritional Biochemistry vol. 4, No. 1 Jan. 1993 pp. 49–57.
Abstract (Corresponding to WO 9214746).

*Primary Examiner*—Johann Richter
*Assistant Examiner*—Kimberly Kestler
*Attorney, Agent, or Firm*—George M. Gould; George W. Johnston; Ellen Ciambrone Coletti

[57] ABSTRACT

The invention comprises compounds of the formula

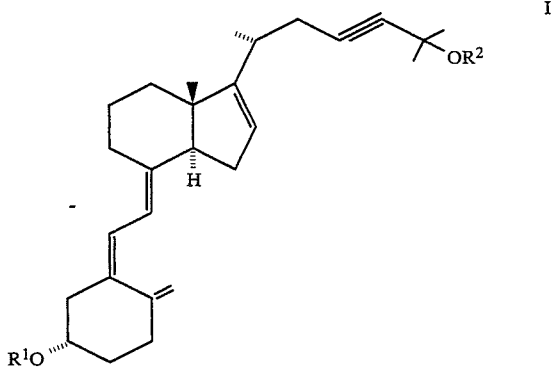

wherein $R^1$ and $R^2$ are hydrogen or acyl; provided that only one of $R^1$ or $R^2$ is hydrogen, useful in the treatment of hyperproliferative skin diseases and sebaceous gland diseases. The invention also includes a process for making these compounds and steroid intermediates of the process.

10 Claims, No Drawings

STEROID INTERMEDIATES FOR THE FORMATION OF VITAMIN D3 ANALOGUES

This is a division of application Ser. No. 08/155,663, filed Nov. 22, 1993, now U.S. Pat. No. 5,342,833, which is a continuation of Ser. No. 07/979,133, filed Nov. 20, 1992, now abandoned.

BRIEF SUMMARY OF THE INVENTION

The invention relates to compounds of the formula

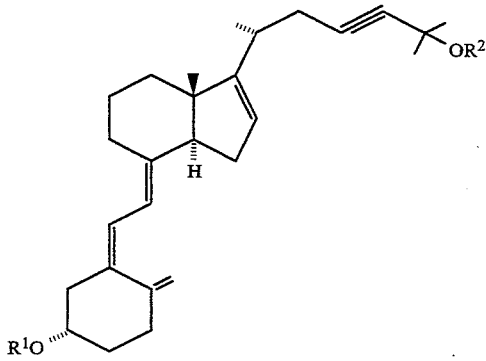

wherein $R^1$ and $R^2$ are hydrogen or acyl; provided that only one of $R^1$ or $R^2$ is hydrogen.

Compounds of formula I as described above are useful as agents for the treatment of hyperproliferative skin diseases such as psoriasis and for the treatment of sebaceous gland diseases such as acne or seborrheic dermatitis.

DETAILED DESCRIPTION OF THE INVENTION

As used herein, the term "acyl" denotes a group of the formula $R^3CO-$ wherein $R^3$ is lower alkyl or aryl, which may be unsubstituted or substituted by one or more substituents selected from the group consisting of lower alkyl, aryl, alkoxy and acyloxy.

As used herein, the term "lower alkyl" denotes a straight or branched-chain alkyl group containing 1 to 4 carbon atoms, for example, methyl, ethyl, propyl, isopropyl, butyl and the like. Alternatively, the number of carbon atoms in an alkyl group is designated herein as in "$C_1-C_3$ alkyl" which denotes a straight or branched-chain alkyl group containing 1 to 3 carbon atoms. The term "aryl" denotes a group derived from an aromatic hydrocarbon.

In the formulas presented herein, the various substituents are illustrated as joined to the nucleus by one of the following notations: a wedged solid line ( ▬ ) indicating a substituent which is above the plane of the molecule, and a wedged dotted line (••••‖) indicating a substituent which is below the plane of the molecule. A wavy line indicates either a α or β orientation.

The invention relates to compounds of the formula

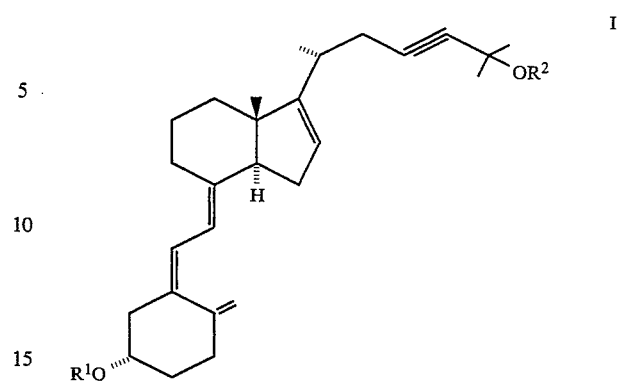

wherein $R^1$ and $R^2$ are hydrogen, or acyl provided that only one of $R^1$ or $R^2$ is hydrogen.

Compounds of formula I as described above stimulate differentiation and decrease proliferation of human keratinocytes. Accordingly, compounds of formula I as described above are useful as agents in the treatment of hyperproliferative skin disorders such as psoriasis, basal cell carcinomas, disorders of keratinization, and keratosis. The compounds of formula I are also useful as agents for the treatment of sebaceous gland diseases such as acne or seborrheic dermatitis.

Preferably in the compounds of formula I, $R^1$ is acyl, preferably $R^3CO$ wherein $R^3$ is lower alkyl or aryl and $R^2$ is hydrogen or acetyl.

Preferred compounds of formula I of the invention include (3β,5Z,7E)-9,10-secocholesta-5,7,10(19),16-tetraen-23-yne-3,25-diol diacetate and (3β,5Z,7E)-9,10-secocholesta-5,7,10(19),16-tetraen-23-yne-3,25-diol 3-(4-phenyl)benzoate.

The compounds of formula I can be prepared as hereinafter described in Reaction Schemes I-IV.

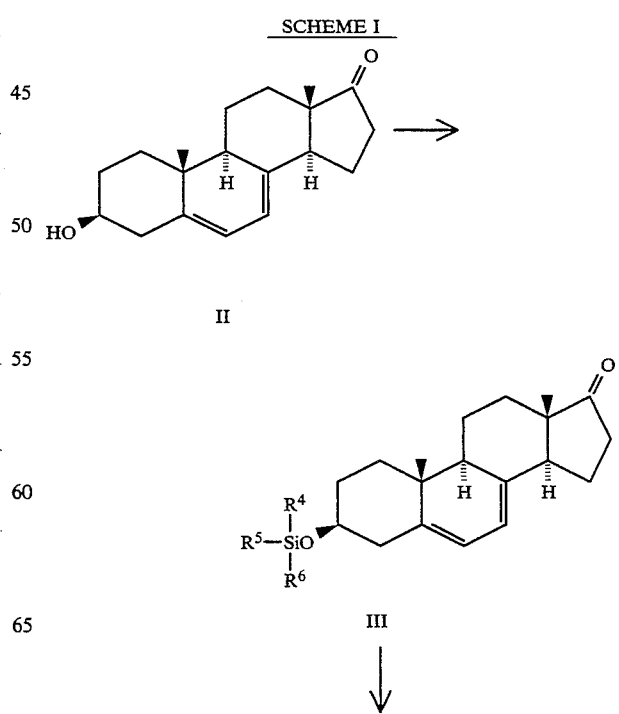

-continued
SCHEME I

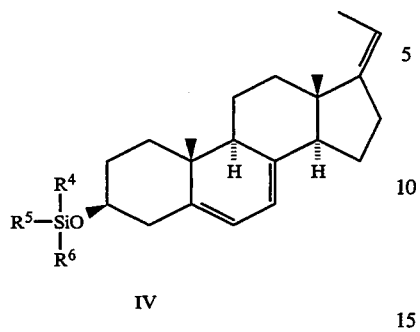

IV wherein $R^4$, $R^5$ and $R^6$ are independently $C_1$–$C_6$ alkyl or phenyl.

In the above formula Scheme I, the compound of formula II, a known compound, is converted to a compound of formula III, by reaction with, for example, trialkylsilyl chloride such as chlorodimethylthexylsilane in an aprotic organic solvent such as, for example, methylene chloride in the presence of a base such as imidazole.

A compound of formula III is reacted with ethylenetriphenylphosphorane in an aprotic organic solvent such as, for example, toluene to yield a corresponding compound of formula IV.

SCHEME II

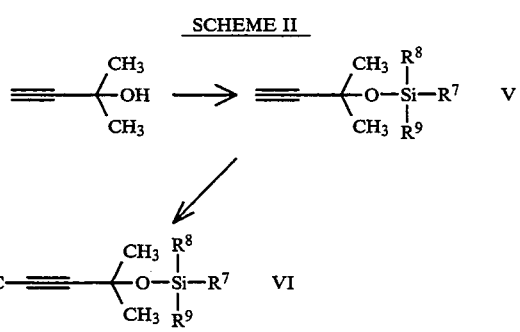

wherein $R^7$, $R^8$, and $R^9$ are independently $C_1$–$C_6$ alkyl or phenyl.

In Scheme II, 3-hydroxy-3-methylbutyne, a known compound, is converted to a compound of formula V by reaction with tert.butyldimethylsilyl chloride in a mixture of N,N-dimethylformamide and imidazole.

The compound of formula V is converted to the corresponding compound of formula VI by reaction with N-butyllithium and N,N-dimethylformamide in anhydrous tetrahydrofuran.

SCHEME III

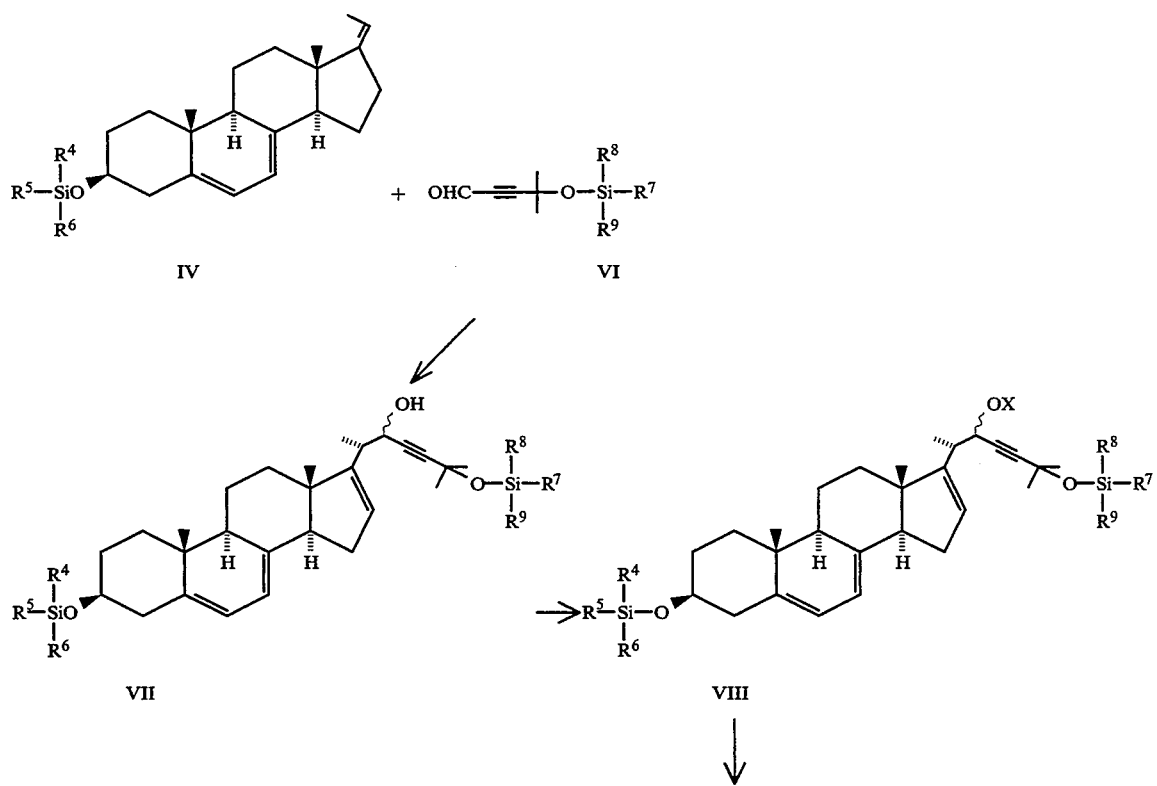

-continued
SCHEME III

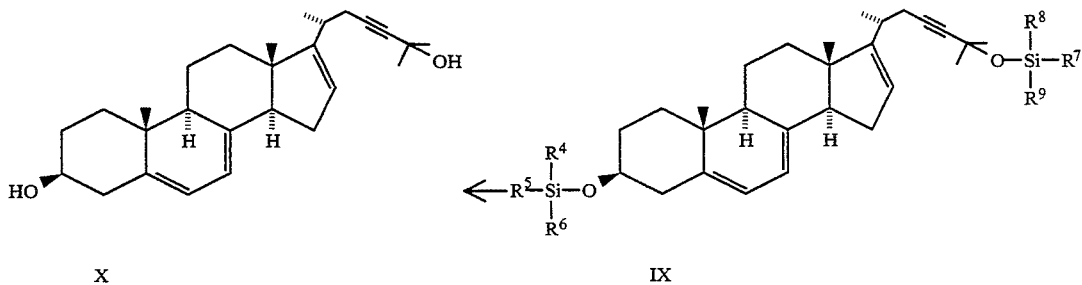

X    IX wherein $R^4$, $R^5$, $R^6$, $R^7$, $R^8$, $R^9$, are independently $C_1$–$C_6$ alkyl or phenyl, X is

wherein $R^{10}$ is

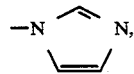

—NHPh, —OPh, —N(CH₃)₂, or —SCH₃.

In formulation scheme III, a compound of formula IV is converted to a corresponding compound of formula VII, by reaction with a compound of formula VI in an aprotic organic solvent, such as, hexane in the presence of a Lewis acid, such as dimethylaluminum chloride.

The compound of formula VII is converted to a compound of formula VII, by reaction with, for example, 1,1'-thiocarbonyldiimidazole, phenyl chlorothionoformate, dimethylthiocarbamoyl chloride, carbon disulfide, or preferably, phenyl isothiocyanate in an aprotic solvent, such as, for example, tetrahydrofuran in the presence of a base, such as, for example, sodium hydride.

The compound of formula VIII is converted to a corresponding compound of formula IX, by reaction with, for example, tributyltin hydride in an aprotic organic solvent, such as, for example, hexane in the presence of a radical initiator such as 2,2'-azobis(2-methylpropionitrile).

The compound of formula IX is reacted with a fluoride salt, such as, for example, tetrabutylammonium fluoride in tetrahydrofuran to give the compound of formula X.

SCHEME IV

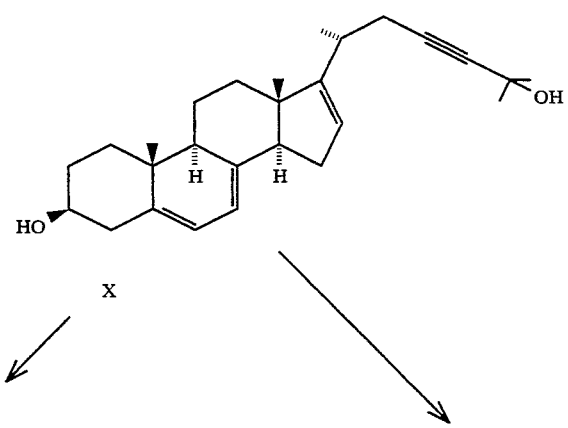

X

-continued
SCHEME IV

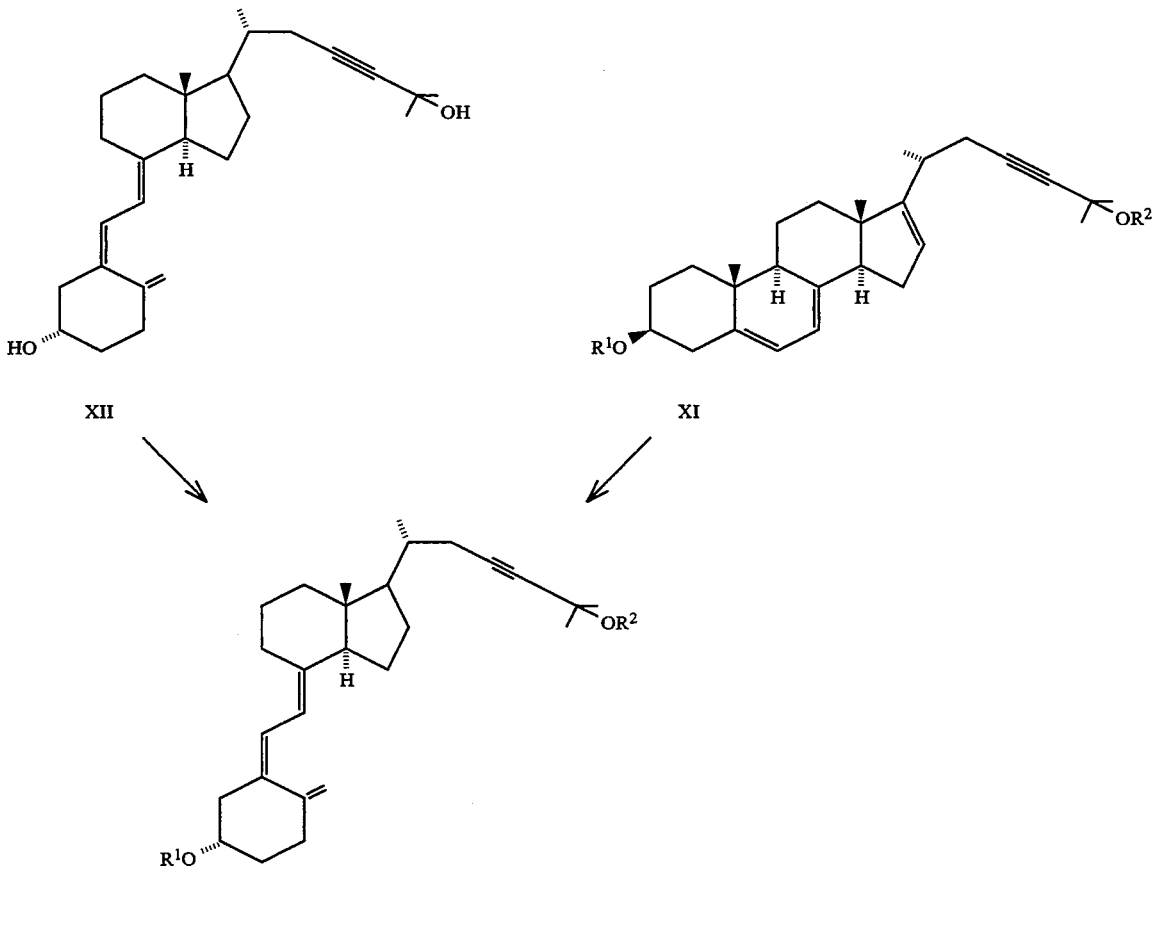

wherein $R^1$ and $R^2$ are independently hydrogen or acyl.

The compound of formula I may be obtained by subjecting the compound of formula X to acylation to give a compound of formula XI, which is then subjected to photolysis and thermal isomerization. The above stated photolysis is carried out preferably by using a medium pressure Mercury lamp in the presence of 4-dialkylaminobenzoate, such as, ethyl 4-dimethylaminobenzoate as a filter to block approximately 290–320 nm light.

Alternatively, the compound of formula I is obtained by subjecting the compound of formula X to the above stated photolysis and thermal isomerization to give a compound of formula XII, which is acylated with, for example, 4-phenylbenzoyl chloride or acetic anhydride in an aprotic solvent, such as, for example, methylene chloride in the presence of a base, such as, for example, triethylamine.

The compounds of formula I as described above can be administered orally, for the treatment of hyperproliferative skin diseases such as psoriasis, basal cell carcinomas, disorders of keratinization, and keratosis, to warmblooded animals which need such treatment. More specifically, the compounds of formula I as described above can be administered orally to an adult human in dosages that are in the range of about 0.1 to 1000 μg per day, preferably about 7 to 70 μg per day for the treatment of hyperproliferative skin diseases such as psoriasis, basal cell carcinomas, disorders or keratinization, and keratosis. These compounds can be administered orally for the treatment of acne in humans at a dosage of about 0.7 to 700 μg per day, preferably 7 to 70 μg per day.

The compounds of formula I as described above can be administered topically, for the treatment of hyperproliferative skin diseases such as psoriasis, basal cell carcinomas, disorders of keratinization, and deratosis, to warmblooded animals which need such treatment. More specifically, the compounds of formula I as described above can be administered topically in dosages that are in the range of about 1 to about 1000 μg per gram of topical formulation per day, for the treatment of hperproliferative skin diseases such as psoriasis, basal cell carcinomas, disorders of keratinization, and keratosis and in the range of about 1 to about 1000 μg per gram of topical formulation per day for the treatment of sebaceous gland diseases such as acne or seborrheic dermatitis.

The useful activity of compounds of formula I as agents for the treatment of hyperproliferative skin diseases can be demonstrated by the following test procedures:

Human Keratinocyte Antiproliferation Assay

Primary or passage one subconfluent cultures of human neonatal keratinocytes grown in Keratinocyte Growth Medium ® (KGM ® modified MCDB 153, Clonetics, Inc. Catalog #CC3001) supplemented with antibiotics or calcium chloride as needed. Cultures were obtained from neonatal foreskin epithelial keratinocytes using standard procedures.

Culture Conditions:

Human neonatal foreskins were collected by circumcision and placed into tubes containing Dulbecco's minimum essential Medium (DMEM) with 10% serum. On arrival at the laboratory, they were mechanically trimmed of excess dermis, and treated with a solution of trypsin/EDTA (0.05%/0.02%) at 4° C. overnight. The epidermis was stripped from the dermis, agitated in buffered saline to remove basal keratinocytes and the stratum corneum later removed. The separated cells were centrifuged, resuspended in media, counted, and the cells plated onto plastic culture dishes or flasks at 10,000 to 25,000 cells/cm$^2$ in KGM medium according to protocols developed by Boyce and Ham, *In Vitro Models for Cancer Research* III., 246–274, (1986) for MCDB 153 medium. The cultures were incubated in humidified chambers with 5% $CO_2$ at 37° C. with re-feeding fresh medium two to three times per week. Prior to reaching confluency, the cells were replated (called passage 1) at 25,000 cells/well on 6-well cluster plates (Costar catalog #3406) in KGM.

Antiproliferation Assay Protocol:

Approximately twenty-four hours after passage, the cells are re-fed with fresh KGM medium supplemented to 1.5 mM $CaCl_2$ that contains test compound or vehicle. Solutions of test compounds were prepared as follows: 1 milligram quantities were received in amber glass vials and stored at −20° C. Sufficient 100% ethanol was added directly to vials to obtain a millimolar solution that was subsequently aliquoted into small amber vials, overlayed with argon gas and stored at −20° C. Each stock solution was thawed once, used and discarded. Stock solutions were used within 4 to 6 weeks. Aliquots from the stock solution were diluted directly into medium and then serially diluted from micromolar to picomolar concentrations. Compounds were typically tested at four concentrations in triplicate wells. Control wells were supplemented with vehicle alone at the highest concentration such as 0.1% ethanol. At the termination of the experiment, prior to the cultures reaching confluency, the cells were enumerated by the following procedure. Dishes were washed with phosphate buffered saline, and then incubated with trypsin/EDTA solution for 30 minutes. Cells were suspended and an aliquot placed into isotonic buffered saline and counted on an electronic particle counter (Coulter Counter). The counter was periodically calibrated for the correct size of keratinocytes. Each well was counted in triplicate. The number of cell/dish was calculated according to dilution factors used and results are presented as percent inhibition from cell numbers obtained in control cultures.

The results are reported as $ED_{50}$ ($\mu M$) value. $ED_{50}$ means the effective dose to inhibit proliferation of 50% of the cells. The $ED_{50}$ for (3$\beta$,5Z,7E)-9,10-secocholesta-5,7,10(19),16-tetraen-23-yne-3,25-diol diacetate was 0.3

1$\alpha$,25-dihydroxycholecalciferol is disclosed in Malloy, et al., page 475, The Journal of Investigative Dermatology, March 1989, Volume 92, Number 3 as an agent for reducing the size of sebaceous glands in the ears of male Syrian hamsters.

The useful activity of compounds of formula I as agents for the treatment of sebaceous gland diseases such as acne or seborrheic dermatitis can be demonstrated by the following test procedure:

II. Hamster Ear Model

The purpose of this test was to evaluate the effect of compounds of the invention on the sebaceous glands of the hamster ear after oral administration of the compounds. Two hundred $\mu l$ of a compound of the invention was dissolved in propylene glycol, administered daily (5 days per week) by gavage to male Golden Syrian hamsters. The animals were sacrificed at 4 weeks and the ears were processed for histological evaluation. The area of the sebaceous glands was measured on histologically prepared cross sections of the ear by image analysis. The data obtained from this study is presented in Table II, below:

TABLE II

| Compound | Dose umoles/kg/day | % Change in Hamster Ear Sebaccous Gland Size Cross. Section Analysis |
|---|---|---|
| (3$\beta$,5Z,7E)-9,10-Secockolesta-5,7,10(19),16-tetraen-23-yne-3,25-diol 3-(4-phenyl)benzoate | 0.105 | −20 |
| | 1.05 | −27 |
| | 10.5 | −31 |
| | 105 | −40 |
| (3$\beta$,5Z,7E)-9,10-Secocholesta-5,7,10(19),16-tetraen-23-yne-3,25-diol diacetate | 0.150 | −18 |
| | 1.5 | −28 |
| | 15 | −37 |
| | 150 | −42 |

The above data demonstrate that compounds of the invention are useful as agents in the treatment of sebaceous gland diseases such as acne or seborrheic dermatitis.

Oral dosage forms comprising compounds of formula I of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include ointments and creams encompassing formulations having oleaginous, adsorbable, water-soluble and emulsion-type bases such as petrolatum, lanolin, polyethylene glycols and the like.

Lotions are liquid preparations and vary from simple solutions to aqueous or hydroalchoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials. In addition to application to the skin, the topical compositions of this invention can also be employed in the treatment of inflammations of mucous membranes, where such membranes are accessible to topical application of medication. For example, the topical composition can be applied to the mucous lining of the mouth or lower colon.

The examples which follow further illustrate the invention.

EXAMPLE 1

Preparation of
($3\beta$)-3-[[(1,1,2-Trimethylpropyl)dimethylsilyl]oxy]androsta-5,7-dien-17-one After a mixture of 149.9 g (523 mmol) ($3\beta$)-3-hydroxy-androsta-5,7-dien-17-one and 56.9 g (836 mmol) imidazole in 500 mL of dichloromethane was cooled to 3° C., 144 mL (732 mmol) dimethylthexylsilyl chloride was added dropwise over 90 min, keeping the temperature below 6° C. After stirring at room temperature overnight, the mixture was washed with 500 mL of water, and the aqueous layer was back-extracted with 200 mL of dichloromethane. The combined organic layers were washed with 500 mL of saturated aqueous NaHCO$_3$, dried over sodium sulfate, and concentrated. The resulting solid was suspended in 700 mL of methanol containing 14 mL of triethylamine, and the suspension was refluxed for 20 minutes. After cooling in a refrigerator overnight, the precipitate was filtered, washed with 600 mL of methanol/H$_2$O (9:1), and dried by suction for 2 hr. Further drying at 40° C. under high vacuum afforded 185.1 g (82.5% yield) of ($3\beta$)-3-[[(1,1,2-trimethylpropyl)dimethylsilyl]oxy]androsta-5,7-dien-17-one as a beige solid: mp 119°–125° C.; Anal. Calcd for C$_{27}$H$_{44}$O$_2$Si: C, 75.64; H, 10.34; Si, 6.55. Found C, 75.82; H, 10.29; Si, 6.72.

EXAMPLE 2

Preparation of
($3\beta$,17Z)-(1,1,2-Trimethylpropyl)(pregna-5,7,17(20)-trien-3-yloxy)dimethylsilane.

A mixture of 240.2 g (647 mmol) (ethyl)triphenylphosphonium bromide, 72.5 g (647 mmol) potassium t-butoxide, and toluene (1 L) was stirred at room temperature for 1 hr. Then, 185 g (430 mmol) ($3\beta$)-3-[[(1,1,2-trimethylpropyl)dimethylsilyl]-oxy]androsta-5,7-dien-17-one was added with the aid of 50 mL of toluene. The temperature was kept below 25° C. by water cooling. After stirring at room temperature overnight, the reaction was quenched with 24.5 mL (430 mmol) of acetic acid. After stirring for 1 hr, the solid was removed by filtration and washed with 600 mL of toluene. The combined filtrate and washes were concentrated. Then 200 mL of methanol was added and the mixture was concentrated again. The residue was dissolved in a mixture of 650 mL methanol, 65 mL water and 650 mL hexane. The methanol/water layer was back-extracted with 325 mL of hexane. The combined hexane layers were concentrated. Then, 200 mL of methanol was added and the mixture was concentrated again. The resulting solid was suspended in 800 mL of methanol containing 8 mL of triethylamine, and the suspension was refluxed for 30 minutes. After cooling in a refrigerator overnight, the precipitate was filtered, washed with 300 mL of cold methanol, and dried by suction for 4 hr. Further drying at 50° C. under high vacuum afforded, 178.1 g (93.7% yield) of ($3\beta$,17Z)-(1,1,2-trimethylpropyl)(pregna-5,7,17(20)-trien-3-yloxy)dimethylsilane as a yellow solid: mp 94°–97° C. [$\alpha$]$_D$ −62.8° (c 0.94, ethanol); Anal. Calcd for C$_{29}$H$_{48}$OSi: C, 79.02; H, 10.98; Si, 6.37. Found C, 78.74; H, 11.23; Si, 6.50.

EXAMPLE 3 a) Preparation of
4-[[(1,1-Dimethylethyl)dimethylsilyl]oxy-4-methyl-2-pentynal

To a solution of 50.0 g (252 mmol) (1,1-dimethylethyl)[(1,1-dimethyl-2-propynyl)oxy]dimethylsilane in 200 mL of tetrahydrofuran (THF) at −70° C. was added 112 mL (280 mmol) of 2.5M butyl lithium (BuLi) in hexanes dropwise over 25 min., keeping the temperature below −55° C. The mixture was stirred for 5 minutes. Then, 50 mL of dimethylformamide (DMF) was added dropwise over 10 minutes. After 15 minutes, the reaction was quenched by the addition of 32 mL of acetic acid (560 mmol). After the mixture was allowed to warm to −20° C., 200 mL of hexane and 200 mL of water were added. The aqueous layer was back-extracted with 100 mL of hexane. The combined organic layers were washed with 200 mL of saturated aqueous NH$_4$Cl solution and then with 200 mL of brine. After drying over sodium sulfate, the solution was concentrated to dryness. Then the residue was distilled through a 10-cm Vigreaux column to give 48.8 g (85.5% yield) of 4-[[(1,1-dimethylethyl)dimethylsilyl]oxy]-4-methyl-2-pentynal: bp 50° C. (0.5 mm Hg).

b) Preparation of (3β)-25-[[(1,1-Dimethylethyl)dimethylsilyl]oxy]-3-[[dimethyl(1,1,2-trimethylpropyl)silyl]oxy]cholesta-5,7,16-trien-23-yn-22-ol A mixture of 57.65 g (131 mmol) (3β,17Z)-(1,1,2-trimethylpropyl)(pregna-5,7,17(20)-trien-3-yloxy)dimethylsilane, 34.11 g (151 mmol) 4-[[(1,1-dimethylethyl)dimethylsilyl]oxy-4-methyl-2-pentynal, and 800 mL hexane was cooled to about −40°0 C. Then, 185 mL (185 mmol) 1M dimethylaluminum chloride in hexane was added dropwise within 30 min. After the dark brown solution was stirred at −40° C. for 30 min, 400 mL of 5% aqueous sodium phosphate dibasic (w/v) was added dropwise, and the mixture was allowed to warm to 5° C. Then, 300 mL of 3N HCl was added dropwise at a temperature of 0°–5° C. followed by 40 g of Celite. After 15 min, the solid was filtered and washed with 400 mL of hexane. The aqueous layer was extracted twice with hexane. The combined hexane solutions were washed successively with water, 10% aqueous NaHCO$_3$, and brine. The hexane layer was dried and concentrated to give 90 g (overweight) of crude (3β)-25-[[(1,1-dimethylethyl) dimethylsilyl]oxy]-3-[[dimethyl(1,1,2-trimethylpropyl)silyl]oxy] cholesta-5,7,16-trien-23-yn-22-ol (5:1 mixture of epimers at C-22) as an orange oil. This crude material was used for the next step.

EXAMPLE 4

Preparation of Phenylcarbamothioic Acid O-[(3β)-25-[[(1,1-Dimethylethyl)dimethylsilyl]oxy]-3-[[dimethyl(1,1,2-trimethylpropyl)silyl]oxy]cholesta-5,7,16-trien-23-yn-22-yl] Ester.

Sodium hydride (60% dispersion, 6.55 g, 164 mmol) was suspended in 200 mL of THF followed by the addition of 446 mg (6.55 mmol) imidazole at 5° C. To this gray suspension, a solution of crude 93 g (131 mmol) (3β)-25-[[(1,1-dimethylethyl)dimethylsilyl]oxy]-3-[[dimethyl(1,1,2-trimethylpropyl)silyl]oxy]cholesta-5,7,16-trien-23-yn-22-ol in 700 mL of THF was added dropwise at 8°–10° C. over 30 min. The resulting dark brown suspension was stirred at the same temperature for 1 h. Then, a solution of 17.3 mL (144 mmol) phenyl isothiocyanate in 200 mL of THF was added, and the mixture was stirred at 10° C. for 1 h. The reaction was quenched by the dropwise addition of 500 mL of 10% aqueous NaHCO$_3$ followed by 70 g of celite. After stirring for 10 minutes, the solid was filtered and washed with 500 ml of ethyl acetate. The aqueous layer was extracted twice with 500 ml each of ethyl acetate. The combined organic layers were washed successively with 10% aqueous NaHCO$_3$ and brine, dried over MgSO$_4$, and concentrated to dryness. Some polar, colored impurities were removed by dissolving 132 g of the residue in 200 mL of 3% ethyl acetate in hexane and filtering it through a plug of 120 g of silica gel. The plug was washed with 1 L of 3% ethyl acetate in hexane. The eluate was collected and concentrated to dryness to give 117 g (overweight) of crude phenylcarbamothioic acid O-[(3β)-25-[[(1,1-dimethylethyl)dimethylsilyl]oxy]-3-[[dimethyl(1,1,2-trimethylpropyl)silyl]oxy]cholesta-5,7,16-trien-23-yn-22-yl] ester as an orange oil. This crude material was used for the next step.

EXAMPLE 5

Preparation of [[(3β)-25-[[(1,1-Dimethylethyl)dimethylsilyl]oxy]-cholesta-5,7,16-trien-23-yn-3-yl]oxy]dimethyl(1,1,2-trimethylpropyl)silane To a mixture of 70.5 mL (262 mmol) tributyltin hydride and 1.08 g (6.55 mmol) 2,2'-azobis(2-methylpropionitrile) (AIBN) in 50 mL of hexane at 80° C. was added a solution of 117 g (131 mmol) crude phenyl-carbamothioic acid O-[(3β)-25-[[(1,1-dimethylethyl)dimethylsilyl]oxy]-3-[[dimethyl(1,1,2-trimethylpropyl)silyl]oxy]cholesta-5,7,16-trien-23-yn-22-yl] ester in 1.5 L of hexane over 45 min. After refluxing for 1 hr, additional tributyltin hydride (35 mL, 131 mmol) and AIBN (1.07 g, 6.52 mmol) were added. After 30 min. of refluxing, the mixture was cooled to room temperature and stirred for 1 hr. The precipitate was filtered, and the filtrate was concentrated. The residue was dissolved in 200 mL of hexane and purified by filtration through 425 g of silica gel. The column was eluted with hexane and then with 20% toluene in hexane. The fractions containing the product were combined and concentrated to give 114 g (overweight) of crude [[(3β)-25-[[(1,1-dimethylethyl)dimethylsilyl]oxy]cholesta-5,7,16-trien-23-yn-3-yl]oxy]dimethyl (1,1,2-trimethylpropyl)silane as a light yellow oil. This crude material was used in the next step. An analytical sample was obtained by chromatographic purification followed by crystallization from ethyl acetate/methanol (1:1): mp 62°–66° C.;Anal. Calcd. for C$_{41}$H$_{70}$O$_2$Si$_2$: C, 75.62, H, 10.84; Si, 8.63. Found C, 75.12; H, 10.77; Si, 8.55

EXAMPLE 6

Preparation of (3β)-Cholesta-5,7,16-trien-23-yne-3,25-diol

To a solution of 114 g (131 mmol) crude [[(3β)-25-[[(1,1-dimethylethyl)dimethylsilyl]oxy]cholesta-5,7,16-trien-23-yn-3-yl]oxy]dimethyl(1,1,2-trimethylpropyl)silane in 500 mL of THF was added 200 g (765 mmol) tetrabutylammonium fluoride hydrate with the aid of 500 mL of THF. After stirring at room temperature for 18 hr., the mixture was diluted with 500 mL of ethyl acetate and 500 mL of 10% aqueous ammonium chloride. The aqueous layer was extracted twice with 500 mL each of ethyl acetate. The combined organic layers were washed with 500 mL of 10% aqueous ammonium chloride, 500 mL of water, and 500 mL of brine. The organic layer was dried over MgSO$_4$ and concentrated to a total weight of 525 g. The resulting suspension was stirred at room temperature for 2 hr and then stored in a freezer overnight. The solid was filtered, washed with cold ethyl acetate, and air-dried for 2 hr to give 27.8 g of crude (3β)-cholesta-5,7,16-trien-23-yne-3,25-diol. This was suspended in 270 mL of methanol and the mixture was refluxed for 10 min. Then, 55 mL waster was added dropwise over 10 min. The suspension was stirred at 60° C. for 1 h, and stored in a refrigerator overnight. The precipitate was filtered, washed with cold 100 mL 50% aqueous methanol, and dried in a vacuum oven at 45° C. to give 25.4 g (49.1% over four steps) of (3β)-cholesta-5,7,16-trien-23-yne-3,25-diol as white crystals: mp 185°–192° C. Anal. Calcd. for C$_{27}$H$_{38}$O$_2$: C, 82.18; H, 9.71. Found: C, 81.93; H, 9.74.

EXAMPLE 7

Preparation of
(3β)-Cholesta-5,7,16-trien-23-yne-3,25-diol Diacetate

To a cold suspension of 75.3 g (191 mmol) (3β)-cholesta-5,7,16-trien-23-yne-3,25-diol in 450 mL of dichloromethane was added 107 mL (1.14 mol) acetic anhydride and 160 mL (1.14 mol) triethylamine. After the suspension was cooled to 2° C., 4.6 g (38 mmol) 4-dimethylaminopyridine was added. After 10 min, the cold bath was removed and the mixture was stirred at room temperature overnight. After cooling again with an ice-water bath, 30.7 mL (758 mmol) methanol was added, and the mixture was stirred at room temperature for 1.5 hr. The mixture was washed with water and the aqueous layer was extracted with dichloromethane. The combined organic layers were washed with 200 mL 1N HCl, and the aqueous layer was extracted with dichloromethane. The combined organic layers were washed with saturated aqueous NaHCO$_3$, dried over Na$_2$SO$_4$, and concentrated to dryness. The residue was dissolved in 700 mL of warm 95% methanol. After a seed crystal was added, the suspension was stored in a refrigerator overnight. The precipitate was filtered and washed with 700 mL of cold 90% methanol. After being dried under high vacuum, 82.05 g (89.8%) of (3β)-cholesta-5,7,16-trien-23-yne-3,25-diol diacetate was obtained as a white solid: mp 98°-101° C. Anal. Calcd. for C$_{31}$H$_{42}$O$_4$: C, 77.79; H, 8.84. Found C, 77.74; H, 8.88.

EXAMPLE 8

Preparation of
(3β,5Z,7E)-9,10-Secocholesta-5,7,10(19),16-tetraen-23-yne-3,25-diol Diacetate A solution of 16.4 g (34.3 mmol) (3β)-cholesta-5,7,16-trien-23-yne-3,25-diol diacetate and 1.64 g ethyl 4-dimethylaminobenzoate in 1.7 L of tert-butyl methyl ether at −20° C. was irradiated with a 450 W medium pressure lamp through a quartz immersion well. During the photolysis, the arc housing was constantly purged with a slow current of nitrogen. After 8 hr of irradiation at 0° to −20° C., a uranium filter was inserted in the arc housing, and then 66 mg of 9-acetylanthracene was added to the solution. After 1 hr 45 min of irradiation through the filter at 0° to −20° C., the solution was allowed to warm to room temperature overnight, and then washed four times with a total of 400 mL of 3N HCl. The organic layer was then washed with 200 mL of saturated aqueous NaHCO$_3$ and dried over Na$_2$SO$_4$. The solution was concentrated to dryness. Then the residual oil was purified by chromatography on silica gel, eluting with 3 L of 7% ethyl acetate in hexane. After discarding about 0.8 L of the eluent, the desired fractions were combined and concentrated to give about 13 g of a clear oil.

A total of five separate and comparable experiments produced 65 g (77%) of the crude photo-product from 84 g of (3β)-cholesta-5,7,16-trien-23-yne-3,25-diol diacetate.

A solution of 65 g (prepared above) of the crude photo-products in 1 L of ethyl acetate was refluxed for 4 hr and then allowed to cool to room temperature overnight. The solution was concentrated. The residual semi-solid was dissolved in 650 mL of hot 95% methanol. The solution was cooled to room temperature and then stored in a refrigerator overnight. The crystalline material was filtered and washed with cold 95% methanol. The crystalline solid was dried under high vacuum for 4 hr to afford 33.0 g (40.2% yield from (3β)-cholesta-5,7,16-trien-23-yne-3,25-diol diacetate) of (3β,5Z,7E)-9,10-secocholesta-5,7,10(19),16-tetraen-23-yne-3,25-diol diacetate as a crystalline solid: mp 94°-95° C. Anal. Calcd. for C$_{31}$H$_{42}$O$_4$: C, 77.79; H, 8.84. Found C, 77.66; H, 8.93.

EXAMPLE 9

Preparation of
(3β,5Z,7E)-9,10-Secocholesta-5,7,10(19),16-tetraen-23-yne-3,25-diol A solution of 18.0 g (45.6 mmol) (3β)-cholesta-5,7,16-trien-23-yne-3,25-diol, 3.6 g ethyl dimethylaminobenzoate, and 1.7 L ethanol at −20° C. was irradiated with a 450 watt medium pressure lamp through a quartz immersion well for 7 hr. A uranium filter was inserted in the arc housing, and then 180 mg of 9-acetylanthracene was added to the solution. After 2 hr. of irradiation through the filter at 0° to −20° C., the solution was allowed to warm to room temperature overnight. The solvent was removed under reduced pressure. The residual ethanol was removed by co-evaporation with toluene. Then, the residue was suspended in 400 mL of toluene. After dilution with 400 mL of hexane, the suspension was stored in a refrigerator overnight. The precipitate was filtered and washed with 200 mL of toluene/hexane (1:1) and then with 400 mL toluene. The combined filtrate and washes were concentrated to about 400 mL of the volume. This solution was stirred at 90°-100° C. (bath temperature) for 2 hr and then allowed to cool to room temperature overnight. The solution was concentrated to dryness and then purified by chromatography on silica gel eluting with 5-10% CH$_3$CN in CH$_2$Cl$_2$ to give 8.35 g (46.4%) of (3β,5Z,7E)-9,10-Secocholesta-5,7,10(19),16-tetraen-23-yne-3,25-diol as a foam. This material was used in the next step without any further purification.

EXAMPLE 10

Preparation of
(3β,5Z,7E)-9,10-Secocholesta-5,7,10(19),16-tetraen-23-yne-3,25-diol 3-(4-Phenyl)benzoate To an ice-cold solution of 8.35 g (21.2 mmol) (3β,5Z,7E)-9,10-Secocholesta-5,7,10(19),16-tetraen-23-yne-3,25-diol, 513 mg (2.1 mmol) 4-dimethylaminopyridine, and 5.3 ml (38.1 mmol) triethylamine in 60 mL of dichloromethane was added 5.99 g (27.5 mmol) (4-phenyl)benzoyl chloride. After stirring at room temperature overnight, the mixture was diluted with 30 ml of dichloromethane and washed with water. The aqueous layer was extracted with dichloromethane. The combined dichloromethane solutions were washed four-times with 200 mL each of saturated aqueous NaHCO$_3$ solution. Each aqueous layer was back-extracted with dichloromethane. The combined organic layers were dried and concentrated. The residue was purified by chromatography on silica gel to give 9.4 g of crude product. This was dissolved in 100 ml of hot methanol, and the solution was slowly cooled to room temperature with stirring. Then the suspension was kept in a refrigerator overnight. The precipitate was filtered and washed with 20 ml of 95% methanol. The solid was dried under high vacuum overnight to give 5.73 g (47.1%) of (3β,5Z,7E)-9,10-secocholesta-5,7,10(19),16-tetraen-23-yne-3,25-diol 3-(4-phenyl)benzoate as a

EXAMPLE 11

4-(tert.butyldimethylsilyl)oxy-4-methyl-pentynal

To the stirred mixture of 25 g (0.29M) of 3-hydroxy-3-methyl-butyne, 50 ml of anhydrous N,N-dimethylformamide and 44.5 g (0.65M) imidazole cooled in an ice-bath was added 50 g (0.33M) tert.butyldimethylsilyl chloride. Stirring in the ice-bath was continued for 15 minutes and then at room temperate overnight. After addition of 250 mg of dimethylaminopyridine, the reaction mixture was heated at 70° C. for two hours and then poured into one liter of cold water. It was then extracted with 5×150 ml of ether. The organic extract was washed with brine, dried over $MgSO_4$ and evaporated to dryness. The crude product was purified by vacuum distillation yielding 3-(tert.butyldimethylsilyl)oxy-3-methyl-butyne.

To the solution of 10 g (50 mmol) of 3-(tert.butyldimethylsilyl)oxy-3-methyl-butyne in 25 ml. of anhydrous tetrahydrofuran cooled at −78° C. in an argon atmosphere was added dropwise over a 40 minute period 40 ml (0.64 mmol) 1.6M solution of N-butyl lithium in hexane, which was followed by addition of 31 ml (400 mmol) of N,N-dimethylformamide. The reaction mixture was stirred for an additional one-half hour at −78° C., and then quenched by addition of ice and pouring into 300 ml of brine. It was then extracted with pentane. The pentane extract was washed with saturated ammonium chloride solution, water and brine, dried over anhydrous sodium sulfate and evaporated to dryness. The crude product was purified by distillation at 113°–115° C./25 mmHg. It gave 8.88 g (78%) of the title compound.

EXAMPLE 12

| WET GRANULATION FORMULATION | | | | |
|---|---|---|---|---|
| Ingredients | mg/tablet | | | |
| 1. (3β,5Z,7E)-9,10-Secocholesta-5,7,10(19),16-tetraen-23-yne-3,25-diol diacetate | 0.1 | 0.5 | 5.0 | 5.0 |
| 2. Lactose Anhydrous DTG | 106.9 | 106.5 | 102.0 | 118.0 |
| 3. Avicel PH 102 | 15.0 | 15.0 | 15.0 | 25.0 |
| 4. Modified Starch | 7.0 | 7.0 | 7.0 | 10.0 |
| 5. Magnesium Stearate | 1.0 | 1.0 | 1.0 | 2.0 |
| TOTAL | 130.0 | 130.0 | 130.0 | 160.0 |

Manufacturing Procedure
1. Dissolve Item 1 in a suitable solvent such as alcohol.
2. Spread the solution in Step 1 over Item 2, dry.
3. Add Items 3 and 4 and mix for 10 minutes.
4. Add magnesium stearate and mix for 3 minutes and compress.

EXAMPLE 13

| CAPSULE FORMULATION | | | | |
|---|---|---|---|---|
| Ingredients | mg/capsule | | | |
| 1. (3β,5Z,7E)-9,10-Secocholesta-5,7,10(19),16-tetraen-23-yne-3,25-diol diacetate | 0.1 | 0.5 | 5.0 | 25.0 |
| 2. Lactose Hydrous | 168.9 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Magnesium Stearate | 1.0 | 1.0 | 1.0 | 2.0 |
| TOTAL | 200.0 | 200.0 | 200.0 | 200.0 |

Manufacturing Procedure
1. Mix Items 1, 2 and 3 in a suitable mixer for 30 minutes.
2. Add Items 4 and 5 and mix for 3 minutes.
3. Fill into suitable capsule.

EXAMPLE 14

| TABLET FORMULATION (WET GRANULATION) | | | |
|---|---|---|---|
| Ingredients | mg/tablet | | |
| | 25 mg | 100 mg | 500 mg |
| 1. (3β,5Z,7E)-9,10-Secocholesta-5,7,10(19),16-tetraen-23-yne-3,25-diol diacetate | 25 | 100 | 500 |
| 2. Lactose Anhydrous DTG | 105 | 30 | 150 |
| 3. Pregelatinized Starch | 6 | 6 | 30 |
| 4. Microcrystalline Cellulose | 30 | 30 | 150 |
| 5. Magnesium Stearate | 1 | 1 | 5 |
| TOTAL | 167 | 167 | 835 |

Manufacturing Procedure
1. Mix Items 1, 2, 3 and 4 and granulate with water.
2. Dry the granulation at 50° C.
3. Pass the granulation through suitable milling equipment.
4. Add Item 5 and mix for three minutes; compress on a suitable press.

EXAMPLE 15

| CAPSULE FORMULATION | | | |
|---|---|---|---|
| Ingredients | mg/tablet | | |
| | 25 mg | 100 mg | 500 mg |
| 1. (3β,5Z,7E)-9,10-Secocholesta-5,7,10(19),16-tetraen-23-yne-3,25-diol diacetate | 25 | 100 | 500 |
| 2. Corn Starch (Pregelatinized) | 83 | 8 | 40 |
| 3. Modified Starch | 4 | 4 | 20 |
| 4. Talc | 4 | 4 | 20 |
| 5. Magnesium Stearate | 1 | 1 | 5 |
| TOTAL | 117 | 117 | 585 |

Manufacturing Procedure
1. Mix Items 1, 2, and 3 and wet granulate with water.
2. Dry the granulation at 45° C. overnight.
3. Mill through a suitable screen using appropriate milling equipment.
4. Add Items 4 and 5 and mix for five minutes.

EXAMPLE 16

| WET GRANULATION FORMULATION | | | | |
|---|---|---|---|---|
| Ingredients | mg/tablet | | | |
| 1. (3β,5Z,7E)-9,10-Secocholesta-5,7,10(19),16-tetraen-23-yne-3,25-diol 3-(4-phenyl) benzoate | 0.1 | 0.5 | 5.0 | 5.0 |
| 2. Lactose Anhydrous DTG | 106.9 | 106.5 | 102.0 | 118.0 |
| 3. Avicel PH 102 | 15.0 | 15.0 | 15.0 | 25.0 |
| 4. Modified Starch | 7.0 | 7.0 | 7.0 | 10.0 | white solid: mp 105°–110° C. Calcd. for $C_{40}H_{46}O_3$: C, 83.58; H, 8.07. Found: C, 83.67; H, 8.17.

-continued

WET GRANULATION FORMULATION

| Ingredients | mg/tablet | | | |
|---|---|---|---|---|
| 5. Magnesium Stearate | 1.0 | 1.0 | 1.0 | 2.0 |
| TOTAL | 130.0 | 130.0 | 130.0 | 160.0 |

Manufacturing Procedure
1) Dissolve Item 1 in a suitable solvent such as alcohol.
2) Spread the solution in Step 1 over Item 2, dry.
3) Add Items 3 and 4 and mix for 10 minutes.
4) Add magnesium stearate and mix for 3 minutes and compress.

EXAMPLE 17

CAPSULE FORMULATION

| Ingredients | mg/tablet | | | |
|---|---|---|---|---|
| 1. (3β,5Z,7E)-9,10-Secocholesta-5,7,10(19),16-tetraen-23-yne-3,25-diol 3-(4-phenyl)-benzoate | 0.1 | 0.5 | 5.0 | 25.0 |
| 2. Lactose Hydrous | 168.9 | 168.5 | 159.0 | 123.0 |
| 3. Corn Starch | 20.0 | 20.0 | 25.0 | 25.0 |
| 4. Talc | 10.0 | 10.0 | 10.0 | 15.0 |
| 5. Magnesium Stearate | 1.0 | 1.0 | 1.0 | 2.0 |
| TOTAL | 200.0 | 200.0 | 200.0 | 200.0 |

Manufacturing Procedure
1) Mix Items 1, 2 and 3 in a suitable mixer for 30 minutes.
2) Add Items 4 and 5 and mix for 3 minutes.
3) Fill into suitable capsule.

EXAMPLE 18

TABLET FORMULATION (Wet Granulation)

| Ingredients | mg/tablet | | |
|---|---|---|---|
|  | 25 mg | 100 mg | 500 mg |
| 1. (3β,5Z,7E)-9,10-Secocholesta-5,7,10(19),16-tetraen-23-yne-3,25-diol 3-(4-phenyl)-benzoate | 25 | 100 | 500 |
| 2. Lactose Anhydrous DTG | 105 | 30 | 150 |
| 3. Pregelatinized Starch | 6 | 6 | 30 |
| 4. Microcrystalline Cellulose | 30 | 30 | 150 |
| 5. Magnesium Stearate | 1 | 1 | 5 |
| TOTAL | 167 | 167 | 835 |

Manufacturing Procedure
1. Mix Items 1, 2, 3 and 4 and granulate with water.
2. Dry the granulation at 50° C.
3. Pass the granulation through suitable milling equipment.
4. Add Item 5 and mix for three minutes; compress on a suitable press.

EXAMPLE 19

CAPSULE FORMULATION

| Ingredients | mg/tablet | | |
|---|---|---|---|
|  | 25 mg | 100 mg | 500 mg |
| 1. (3β,5Z,7E)-9,10-Secocholesta-5,7,10(19),16-tetraen-23-yne-3,25-diol 3-(4-phenyl)-benzoate | 25 | 100 | 500 |
| 2. Corn Starch (Pregelatinized) | 83 | 8 | 40 |
| 3. Modified Starch | 4 | 4 | 20 |
| 4. Talc | 4 | 4 | 20 |

-continued

CAPSULE FORMULATION

| Ingredients | mg/tablet | | |
|---|---|---|---|
|  | 25 mg | 100 mg | 500 mg |
| 5. Magnesium/Stearate | 1 | 1 | 5 |
| TOTAL | 117 | 117 | 585 |

Manufacturing Procedure
1. Mix Items 1, 2, and 3 and wet granulate with water.
2. Dry the granulation at 45° C. overnight.
3. Mill through a suitable screen using appropriate milling equipment.
4. Add Items 4 and 5 and mix for five minutes.

We claim:
1. A compound of the formula

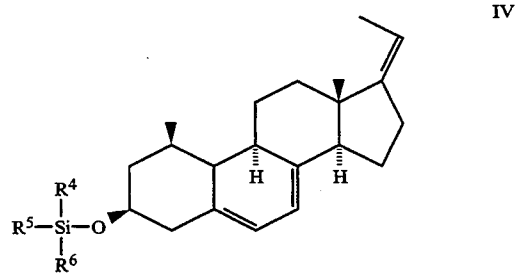

IV wherein $R^4$, $R^5$ and $R^6$ are independently $C_1$–$C_6$ alkyl or phenyl.

2. The compound of claim 1, wherein $R^4$ and $R^5$ are methyl and $R^6$ is thexyl.

3. A compound of the formula

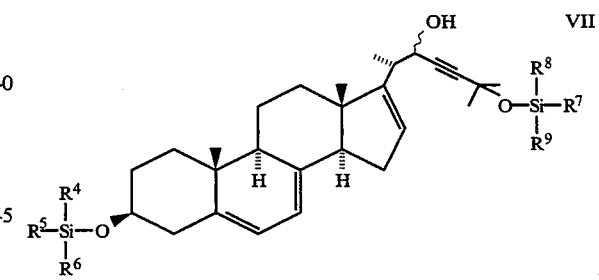

VII wherein $R^4$, $R^5$, $R^6$, $R^7$, $R^8$ and $R^9$ are independently $C_1$–$C_6$ alkyl or phenyl.

4. The compound of claim 3, wherein $R^4$, $R^5$, $R^7$ and $R^8$ are methyl, $R^6$ is thexyl, $R^9$ is tert-butyl.

5. A compound of the formula

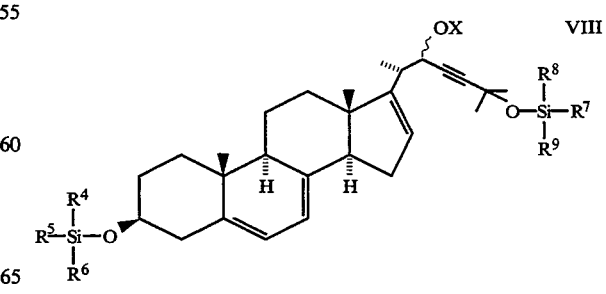

VIII wherein $R^4$, $R^5$, $R^6$, $R^7$, $R^8$ and $R^9$ are independently $C_1$–$C_6$ alkyl or phenyl and X is wherein $R^{10}$ is

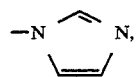

—NHPh, —OPh, —N(CH$_3$)$_2$, or —SCH$_3$, and Ph is phenyl.

6. The compound of claim 5, wherein $R^4$, $R^5$, $R^7$ and $R^8$ are methyl, $R^6$ is thexyl, $R^9$ is tert-butyl, $R^{10}$ is —NHPh and Ph is phenyl.

7. A compound of the formula

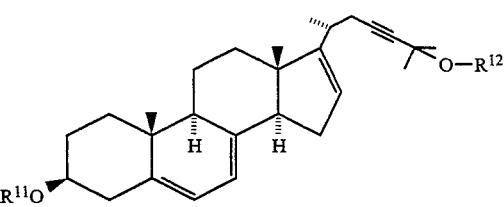

wherein $R^{11}$ and $R^{12}$ are independently

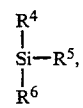

hydrogen or acyl, $R^4$, $R^5$ and $R^6$ are independently C$_1$–C$_6$ alkyl or phenyl.

8. The compound of claim 7, wherein $R^{11}$ is dimethylthexylsilyl and $R^{12}$ is tert-butyldimethylsilyl.

9. The compound of claim 7, wherein $R^{11}$ and $R^{12}$ are hydrogen.

10. The compound of claim 7, wherein $R^{11}$ and $R^{12}$ are acetyl.

* * * * *